United States Patent
Herrera

(10) Patent No.: US 11,931,351 B2
(45) Date of Patent: Mar. 19, 2024

(54) (S)-3-[1-METHYLPYRROLIDIN-2-YL]PYRIDINE, ANALOGUES THEREOF, PRECURSORS THEREOF, OR ITS DERIVATIVES, FOR THE USE AS A PHARMACEUTICAL IN FORM OF A PARENTERAL ADMINISTRATION AND A PROCESS FOR THE PREPARATION OF AN INJECTABLE SUBSTANCE

(71) Applicant: Arturo Solis Herrera, Aguascalientes (MX)

(72) Inventor: Arturo Solis Herrera, Aguascalientes (MX)

(*) Notice: Subject to any disclaimer, the term of this patent is extended or adjusted under 35 U.S.C. 154(b) by 245 days.

(21) Appl. No.: 17/108,972

(22) Filed: Dec. 1, 2020

(65) Prior Publication Data

US 2021/0161878 A1 Jun. 3, 2021

(30) Foreign Application Priority Data

Dec. 2, 2019 (LU) ........................... 101511

(51) Int. Cl.
| | | |
|---|---|---|
| *A61K 31/4439* | (2006.01) | |
| *A61K 9/00* | (2006.01) | |
| *A61K 9/10* | (2006.01) | |
| *A61P 31/16* | (2006.01) | |
| *A61P 35/00* | (2006.01) | |
| *C07D 401/04* | (2006.01) | |

(52) U.S. Cl.
CPC ........ *A61K 31/4439* (2013.01); *A61K 9/0019* (2013.01); *A61K 9/10* (2013.01); *A61P 31/16* (2018.01); *A61P 35/00* (2018.01)

(58) Field of Classification Search
None
See application file for complete search history.

(56) References Cited

U.S. PATENT DOCUMENTS

| | | |
|---|---|---|
| 2002/0069518 A1 | 6/2002 | Girard et al. |
| 2005/0226920 A1 | 10/2005 | Voelker |

FOREIGN PATENT DOCUMENTS

| | | | | |
|---|---|---|---|---|
| EP | 2184066 A1 | | 5/2010 | |
| WO | WO 99/15171 | * | 4/1999 | ........... A61K 31/465 |
| WO | WO 2019/121649 A1 | * | 6/2019 | ........... C07D 401/04 |

OTHER PUBLICATIONS

Lucchesi et al., Clinical Pharmacology and Therapeutics (1967), 8(6), pp. 789-796.*
Han et al., Antinociceptive effect of nicotine in various pain models in the mouse, Arch Pharm Res. Feb. 2005;28(2):209-15.
Glennon, Nicotine and Pain, Medicinal Chemistry Research vol. 13, pp. 74-77(2004).
Pavia et al., Antimicrobial activity of nicotine against a spectrum of bacterial and fungal pathogens, J Med Microbiol. Jul. 2000;49(7):675-6.
Search Report and Written Opinion for LU Application No. LU101511 dated Oct. 7, 2020, 9 pages.

* cited by examiner

*Primary Examiner* — Brian J Davis
(74) *Attorney, Agent, or Firm* — Michael J. Blessent; Bret E. Field; Bozicevic, Field & Francis LLP

(57) ABSTRACT

The invention relates to a (S)-3-[1-Methylpyrrolidin-2-yl] pyridine analogues thereof, precursors thereof, or its derivatives, for the use as a pharmaceutical in form of a substance as a colloid of fine solid and/or liquid particles in a fluid. 1. According to the invention the substance is dispensed in form of a parenteral administration into a human and/or animal body.

23 Claims, 6 Drawing Sheets

Figure 1:
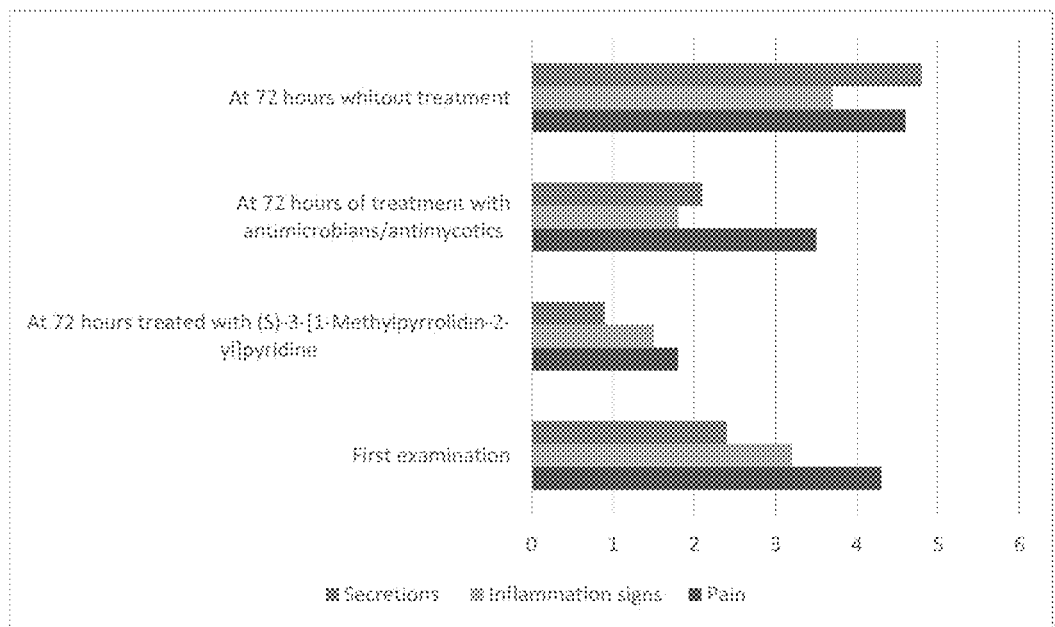

(S)-3-[1-METHYLPYRROLIDIN-2-YL]PYRIDINE, ANALOGUES THEREOF, PRECURSORS THEREOF, OR ITS DERIVATIVES, FOR THE USE AS A PHARMACEUTICAL IN FORM OF A PARENTERAL ADMINISTRATION AND A PROCESS FOR THE PREPARATION OF AN INJECTABLE SUBSTANCE

The present invention relates to a (S)-3-[1-Methylpyrrolidin-2-yl]pyridine, analogues thereof, precursors thereof, or its derivatives—containing pharmaceutical in form of a substance as a colloid of fine solid and/or liquid particles in a fluid for dispensing in form of a parenteral administration into a human and/or animal body. In addition the invention relates to a process for the preparation of an injectable substance.

FIELD OF INVENTION (S)-3-[1-Methylpyrrolidin-2-yl]pyridine, analogues thereof, precursors thereof, or its derivatives, also known as nicotine, is an alkaloid found predominantly in plants like tobacco and cocoa and in lower quantities even in plants like tomato, potato, eggplant and green pepper, all belonging to the nightshade family of plants (Solanaceae). (S)-3-[1-Methylpyrrolidin-2-yl]pyridine is accumulated in the leaves of these plants while its biosynthesis is taken place in the particular roots. Thereby, (S)-3-[1-Methylpyrrolidin-2-yl]pyridine constitutes approximately 0.6 to 0.3% of the dry weight of for example the tobacco plant and is present in the range of 2 to 7 µg/KG of various edible plants.

Further, (S)-3-[1-Methylpyrrolidin-2-yl]pyridine is a stimulant drug acting as an agonist to most nicotinic acetylcholine receptors (nAChR). In lesser doses of approximately 1 mg the substance adds on as a stimulant in mammals, while high amounts of approximately 50 to 100 mg can start being harmful.

(S)-3-[1-Methylpyrrolidin-2-yl]pyridine is hygroscopic, oily, colorless or pale yellow liquid, which is miscible with water and in its base form comprises a pyridine odor. (S)-3-[1-Methylpyrrolidin-2-yl]pyridine comprises a molecular weight of approximately 172 g/mol, is readily soluble in alcohol, ether or light petroleum. Further, (S)-3-[1-Methylpyrrolidin-2-yl]pyridine forms salts with acids that are solid and water soluble. The substance is further absorbed from the blood or muscles or the subcutaneous layers of the skin. Thereby, (S)-3-[1-Methylpyrrolidin-2-yl]pyridine undergoes extensive first pass metabolism when injected. Furthermore, (S)-3-[1-Methylpyrrolidin-2-yl]pyridine easily penetrates the skin, particularly the mucosa. The substance is able of being quickly distributed throughout the bloodstream and is even able to cross the blood-brain-barrier. The half-life of (S)-3-[1-Methylpyrrolidin-2-yl]pyridine in the body is approximately two hours.

(S)-3-[1-Methylpyrrolidin-2-yl]pyridine mentioned within the scope of the invention is always understood as (S)-3-[1-Methylpyrrolidin-2-yl]pyridine itself, analogues thereof, precursors thereof, its derivatives or nicotine which mimic the effect of (S)-3-[1-Methylpyrrolidin-2-yl]pyridine, either alone or in combination with other active substances can be used.

BACKGROUND OF THE INVENTION

In US 20050226920 A1 an injection system with a solution of anticholinergic medications to alleviate the symptoms of nicotine withdrawal is disclosed. Thereby the system is used in conjunction with pre injection and post injection counseling and as a result smoking cessation rates are significantly improved. However, US 20050226920 A1 does not disclose a system wherein (S)-3-[1-Methylpyrrolidin-2-yl]pyridine is administered but rather anticholinergic substances are used.

DETAILED DESCRIPTION OF THE INVENTION

This problem is solved according to the invention by all features of claim 1. The depending claims specify embodiments. Further, this problem is also solved by all features of claim 11 wherein the dependent claims specify possible embodiments.

The special benefit of this invention is that a certain dosage of (S)-3-[1-Methylpyrrolidin-2-yl]pyridine, analogues thereof, precursors thereof or its derivatives, can be administered and reliably delivered to the desired destination within the body.

Advantageously, a parenteral administration can contain divers concentrations of (S)-3-[1-Methylpyrrolidin-2-yl]pyridine, analogues thereof, precursors thereof or its derivatives, in order to be absorbed by the body. A possible administration by which a drug is taken into the body are generally classified by the location at which the substance is applied. A parenteral administration is applied to a human and/or animal body wherein the delivery uses a route other than the gastrointestinal tract. Advantageously, the active substance is not absorbed by the gastrointestinal tract but directly delivered to the target.

In one preferred embodiment of the invention (S)-3-[1-Methylpyrrolidin-2-yl]pyridine is intended to be injected by using a syringe and a hollow needle, which is pierced through the skin to a sufficient depth for the material to be administered into the body. Preferably by an injection. The term injection encompasses intravenous, intramuscular and subcutaneous administration. Advantageously the course of action of injections occurs with an onset of action in approx. 15 to 30 seconds for intravenous injections. In contrast the course of action of an intramuscular injection takes approx. 10 to 20 minutes and for a subcutaneous administration approx. 15 to 30 minutes. As a further advantage active substances applied as an injection have approx. 100% bio-availability. Further this administration can be used for drugs that are poorly absorbed or ineffective when given orally. For the application of an injection an infusion is used by a syringe with a hollow needle, which is pierced through the skin to a sufficient depth for the material to be administered into the body. Thereby the injection follows a parenteral route of administration. Advantageously (S)-3-[1-Methylpyrrolidin-2-yl]pyridine can be injected or infused using one of the following methods: intradermal, subcutaneous, intramuscular, intravenous, intraosseous, intraperitoneal, intrathecal, epidural, intracardiac, intraarticular, intracavernous, and intravitreal, depot injections (long-acting forms of subcutaneous/intramuscular injection). A depot injection is an injection, usually subcutaneous or intramuscular, of a pharmacological agent which releases its active compound in a consistent way over a long period of time.

In one possible embodiment of the invention (S)-3-[1-Methylpyrrolidin-2-yl]pyridine, analogues thereof, precursors thereof or its derivatives, is intended for an intravenous or intramuscular injection. Intravenous therapy is the infusion of liquid substances directly into a vein. Compared with other routes of administration, the intravenous route is the fastest way to deliver fluids and medications throughout the body. Intramuscular injection is the injection of a substance directly into a muscle. Depending on the chemical properties of the drug, the medication may either be absorbed fairly quickly or more gradually. A subcutaneous injection is administered into the subcutis, the layer of skin directly below the dermis and epidermis, collectively referred to as the cutis. Subcutaneous injections are highly effective in administering vaccines and medications. The application of the substances into vein, the muscle or subcutaneously allows an uptake into the bloodstream where the substance can affect the organism and thereby reduce the symptoms of diverse diseases. It is an advantage of an application that no digestion is required. The substance is directly transferred via the bloodstream to the predetermined pharmacological target location.

Advantageously, (S)-3-[1-Methylpyrrolidin-2-yl]pyridine, analogues thereof, precursors thereof or its derivatives, is intended to be administered as a fluid containing a vehicle substance, particularly saline solution. Thereby, (S)-3-[1-Methylpyrrolidin-2-yl]pyridine is a formulation, which is soluble in or miscible with a liquid carrier. Another advantage is that the substance is soluble or miscible at room temperature. Alternatively and/or additionally, (S)-3-[1-Methylpyrrolidin-2-yl]pyridine may be in form of a salt, which is solid at room temperature but can be dissolved in the liquid carrier, particularly in water. Therefore, (S)-3-[1-Methylpyrrolidin-2-yl]pyridine like its salt formulations are generally soluble in water. A process of mixing can occur in order to generate a homogeneous liquid mixture. Beneath (S)-3-[1-Methylpyrrolidin-2-yl]pyridine also pharmacological analogues or derivatives or substances which mimic the effect of (S)-3-[1-Methylpyrrolidin-2-yl]pyridine, either alone or in combination with other active substances can be used. In order to produce a substance for a pharmacological treatment with a parenteral administration, particularly an injection, a combination of (S)-3-[1-Methylpyrrolidin-2-yl]pyridine, a salt and/or sugar and a liquid carrier preferably consisting of water and/or alcohol is used in order to generate (S)-3-[1-Methylpyrrolidin-2-yl]pyridine suitable for the intravenous or intramuscular or subcutaneous delivery. As another additive lactose can be used, which is also soluble in a liquid carrier. The preferred liquid carrier is water. Other liquid carriers can also be used, for example alcohols, preferably in combination with water.

In one special embodiment of the invention (S)-3-[1-Methylpyrrolidin-2-yl]pyridine, analogues thereof, precursors thereof or its derivatives comprise a concentration of 0.3 mg/ml to 4.5 mg/ml, preferably 1.5 mg/ml to 3.0 mg/ml. The concentration of the active agent further depends on the liquidity at room temperature (approximately 20° C.) and/or the temperature of the body (approximately 36° C.). Herein, the delivery system applies a dose of the active agent of about 0.3 mg/ml to 4.5 mg/ml per unit dose. Preferably, 1.5 mg/ml to 3.0 mg/ml is applied. Advantageously, the applied concentration of (S)-3-[1-Methylpyrrolidin-2-yl]pyridine is not toxic. Using a cytotoxic compound can result in a variety of cell fates. The appearance of cytotoxic concentrations can result in necrosis (loss of membrane integrity) and thereby cell lysis, stopping cell growth and dividing or even apoptosis. In order to investigate the cytotoxicity level of certain substances cytotoxicity assays are widely used in the pharmaceutical industry. Further indicators being investigated in order to determine the level of cytotoxicity are for example TNFα (tumor necrosis factor alpha), IFNγ (Interferon gamma) or IL-6 (interleukin). TNFα is a cell signaling protein mainly involved in systemic inflammation. Cells that produce TNFα are mainly macrophages, lymphocytes, mast cells, or neurons. However, the main function of TNFα is in the regulation of immune cells. Further, IFNγ is a soluble cytokine. IFNγ is a cytokine that is critical for immunity against viral, bacterial and protozoal infections. Thereby it is an important activator of macrophages and inducer of MHC (major histocompatibility complex) expression. IFNγ has antiviral, immunoregulatory and anti-tumor properties. Further IL-6 is an interleukin that acts as both a pro-inflammatory cytokine and an anti-inflammatory myokine. In mammalian IL-6 is secreted by T-cells and macrophages to stimulate an immune response.

Advantageously, (S)-3-[1-Methylpyrrolidin-2-yl]pyridine, analogues thereof, precursors thereof or its derivatives, triggers stimulation of cholinergic receptors, particularly nicotinic receptors. Nicotine acetylcholine receptors (nAChR) are neuronal receptor proteins that signal upon a chemical stimulus. The cholinergic receptors are forming ligand gated ion channels in the plasma membrane of the certain neuron. They are expressed on the presynaptic and postsynaptic side of the neuro muscular junctions. As neurotropic receptors they are directly linked to ion channels and thereby are not dependent on second messengers. Neuron receptors are found in the central nervous system as well as in the peripheral nervous system of mammalians. Generally, ligand gated ion channels require the binding of a chemical messenger for opening. The endogenous agonist is acetylcholine wherein they are also triggered by (S)-3-[1-Methylpyrrolidin-2-yl]pyridine, analogues thereof, precursors thereof or its derivatives. The action that (S)-3-[1-Methylpyrrolidin-2-yl]pyridine binds to nicotine cholinergic receptors can be regarded as a key energy source of the cell, as this is responsible for upregulating of energy. All nicotine cholinergic receptors produce excitatory postsynaptic effects. Thereby, energy is upregulated previous to an excitatory postsynaptic effect. Further, the administration of (S)-3-[1-Methylpyrrolidin-2-yl]pyridine upregulates the release of endogenous alpha-MSH. The melanocytes stimulating hormone (MSH) belong to peptide hormones that are produced in the central nervous system. These hormones stimulate the production inducing melanin by melanocytes in the skin and in the hair. Alpha-MSH induces multiple responses in nearly all cells of mammalians, thereby significantly improving and also maintaining good health conditions. Alpha-MSH is further related to chemical energy levels within the mammalian body and thereby fundamental for an optimal body performance.

In one advantageous embodiment of the invention is (S)-3-[1-Methylpyrrolidin-2-yl]pyridine, analogues thereof, precursors thereof or its derivatives is used for the treatment of diseases related to pain. Further, these substances also modulate many disease pathologies like skin physiology, melanocytes function, nerve regeneration, behavior and learning as well as memory, obesity and energy metabolism, brain inflammation, autoimmune diseases, septic shock, endotoxemia, renal ischemic occlusion and reperfusion, mesenteric occlusion and reperfusion, diabetes, viral related diseases like H1N1 intoxications, viral related intoxications like Ebola, congenital mal formations and cancer as well as inflammatory diseases. Particularly, the substance is related to diseases as joint pain and further to diseases related to nerves as well as to skin. Mainly, these diseases can be treated in mammalians preferably in humans and/or animals.

Advantageously, (S)-3-[1-Methylpyrrolidin-2-yl]pyridine, analogues thereof, precursors thereof or its derivatives, are administered every 24 hours. Preferably, the substance is administered every 12 hours, preferably every 6 hours.

Thereby, the frequency of administration depends upon the variety of disease. In administration every 2 to 3 hours is likewise possible.

In a further advantage (S)-3-[1-Methylpyrrolidin-2-yl]pyridine analogues thereof, precursors thereof, or its deviates can be administered with a pre-filled syringe. Advantageously pre-filled syringes contain a single dosage of the active substance. Further pre-filled syringes can be generated for the use of the individual itself, without the help of health personnel. Thereby the advantage occurs that no medical qualifications are necessary.

The present invention further relates to a process for the preparation of parental preparations, which is distributed according to conventional methods. Generally parenteral preparations are sterile preparations containing one or more active ingredients. For the sterilization a steam sterilization for example by use of an autoclave is preferred particularly for aqueous preparations. Parental preparations are intended for administration by injection, infusion or implantation into the body. Advantageously they are packaged in single dosage portions. Further also multi dosage containers are possible. Thereby a single dosage contains a concentration of 0.3 mg/ml to 4.5 mg/ml. Preferably the concentration is 1.5 mg/ml to 3.0 mg/ml. A preferred amount of administered substance is thereby 100 to 1000 ml. Preferably 250 to 750 ml are applied. Most preferably a single dosage contains 500 ml. The amount of application is thereby dependent on the site of application as well as on the site of pharmacological action. A preferred administration is at dose of 1 to 10 drops per minute, preferably of 1 to 5 drops per minute, particularly preferably of 2 to 3 drops by minute. A preferably small amount of to be applied substance is preferred in order to reduce any inconveniences or pain during administration. Further parenteral preparations can comprise solvents, substances to enhance solubility, suspending agents, buffering agents, substances to make the preparation isotonic with blood, stabilizers or antimicrobial preservatives. Advantageously the amount of additional excipients is reduced to a minimum. Further it is preferred when the used additives do not affect the stability, bioavailability, safety or efficacy of the active ingredient. Further a toxicity or local irritations are to be avoided. Commonly water is used for injections as a vehicle. Further also non-aqueous injections are possible wherein preferably oils of vegetable origin are used. Another advantage is to render the parental preparations isotonic by for example sodium chloride. Further to avoid any oxidation the preparation could be performed in an atmosphere of suitable sterile inert gas, such as nitrogen. Further the air in the container can also be replaced by this gas. Further condition which should be monitored are bacterial endotoxins, pH and clarity of the solution.

The present invention is further described in detail with respect to the accompanying examples and figures. Features discussed with the description of the examples and the figures can be freely combined with each other. The features mentioned in the claims and specifications are essential to the invention, either in themselves or in given combination.

EXAMPLES AND FIGURES

In a first example a treatment with (S)-3-[1-Methylpyrrolidin-2-yl]pyridine of viral diseases like for example H1N1 was tested on chicken, infected with the H1N1 virus. Therefore, 30000 diseased chicken were divided into two groups of 15000. One group was treated with (S)-3-[1-Methylpyrrolidin-2-yl]pyridine at doses of 0,002 mg/kg each 24 hours. The other group represented the control group. 24 hours after treatment the treated group began to lay off eggs in contrary to the control group, which turned down the production of eggs. The treatment against intoxication was tested related to mercury, CN, cadmium, arsenic, herbicides, pesticides. As an example mercury poisoning induces a generalized failure, typical to low levels of energy, so that the mortality level is high. As a result 6 in 8 rats died at the dose of 4.5 mg/kg of mercury (HgHCl). In any of the organs edema and hemorrhage was examined. After a treatment of 0, 0937 mg/ml with (S)-3-[1-Methylpyrrolidin-2-yl]pyridine mortality was reduced to 0, 625 of 8 rats.

Figure 2A:
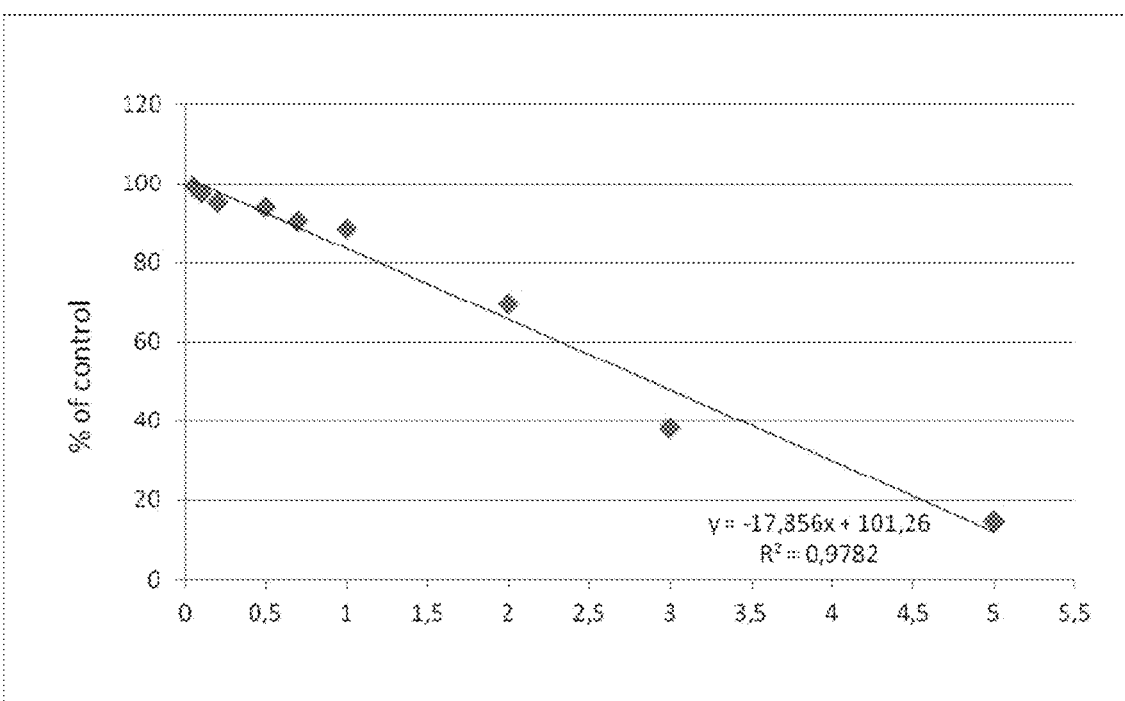
Figure 2B:
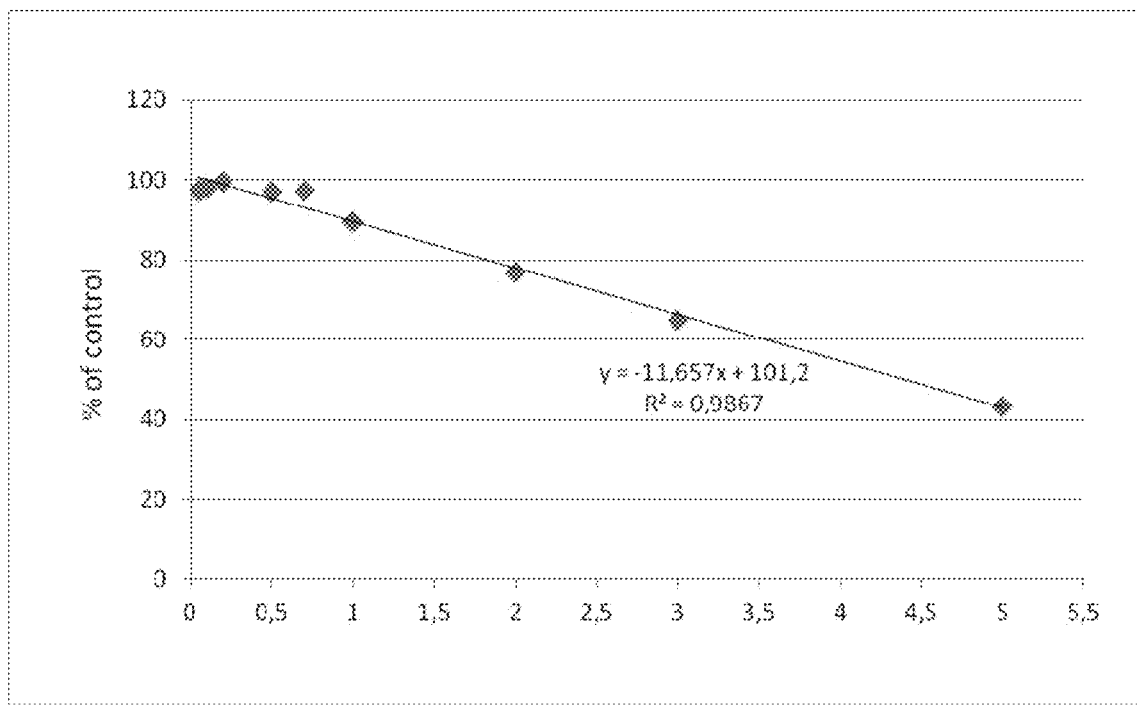
Figure 2C:
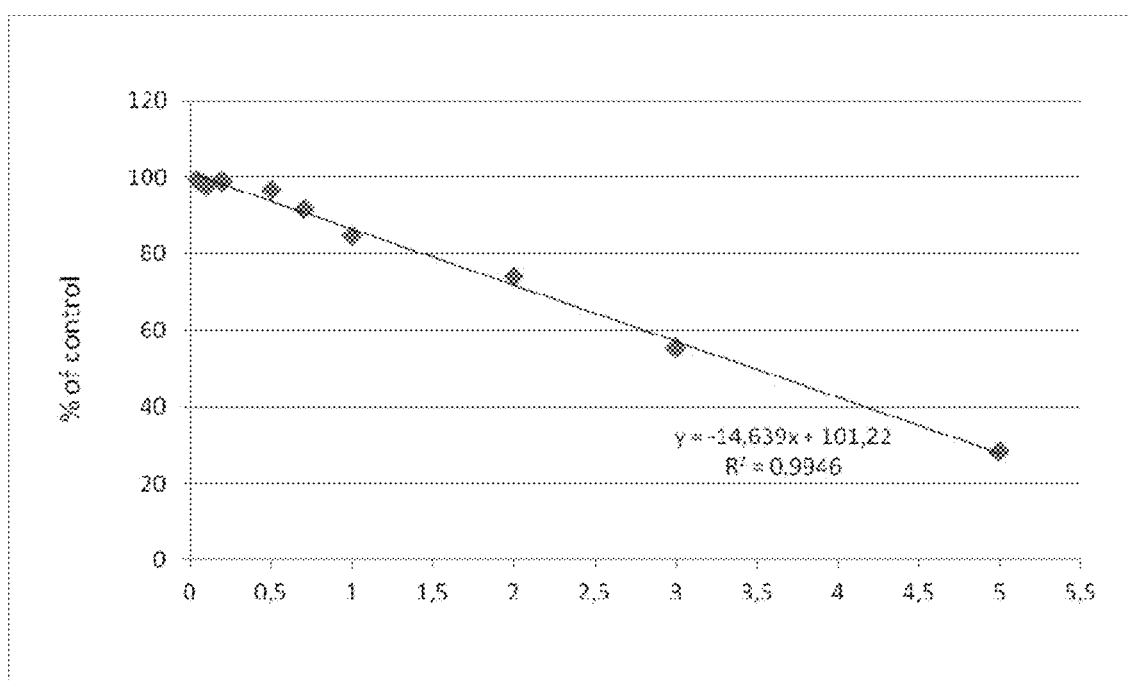
Figure 3:
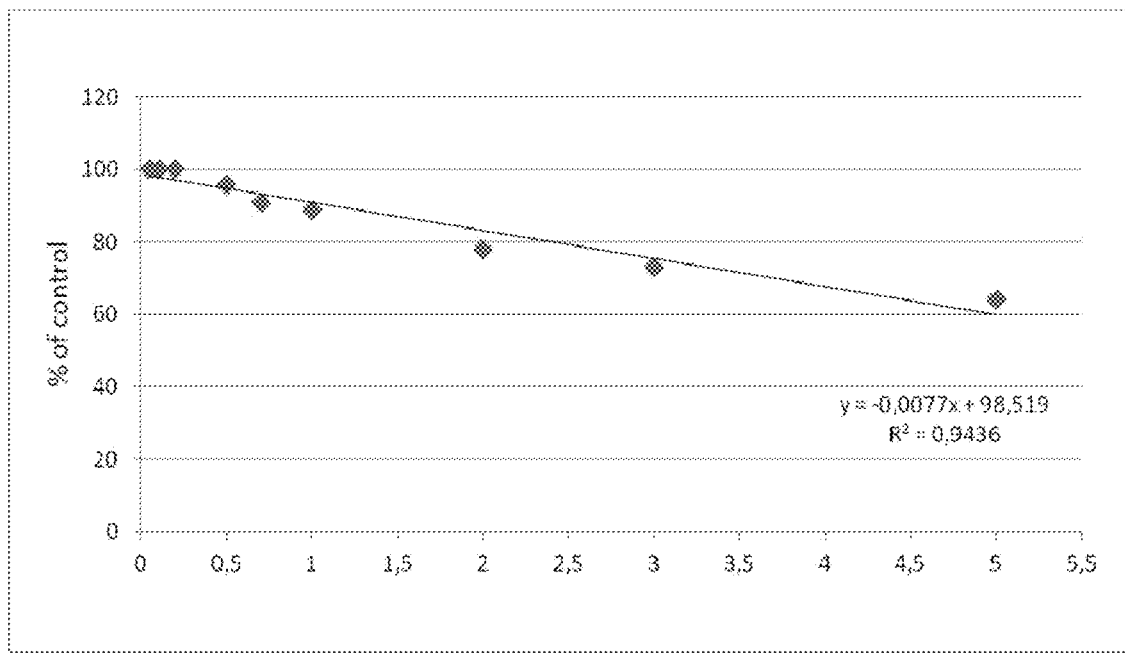
Figure 4A:
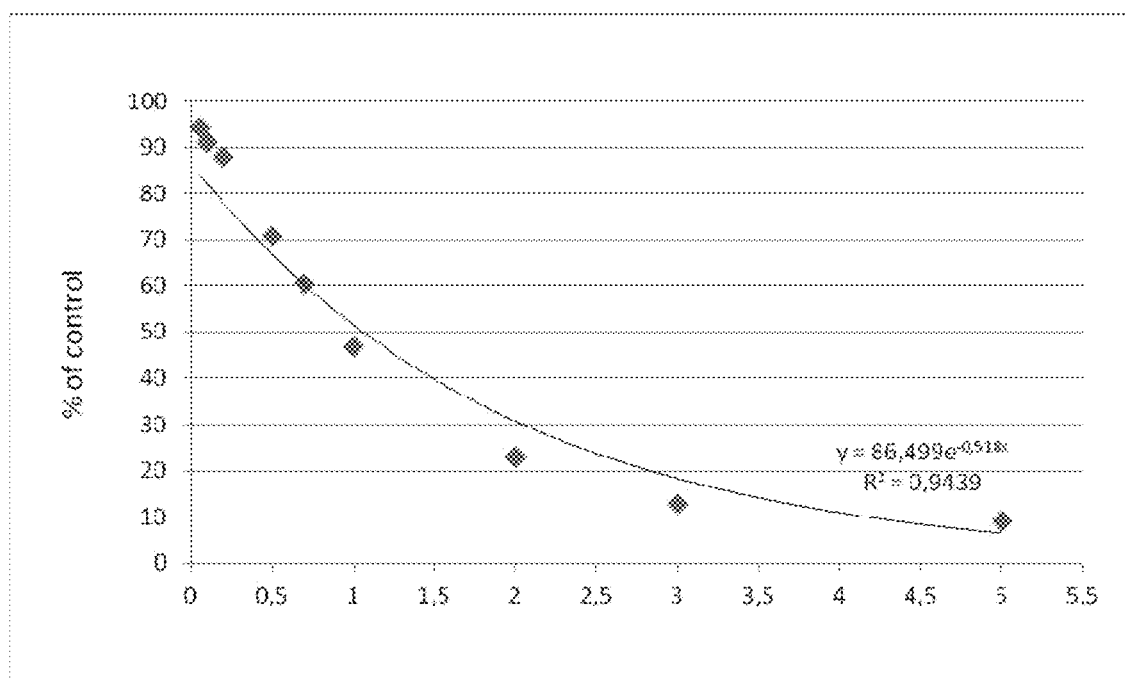
Figure 4B:
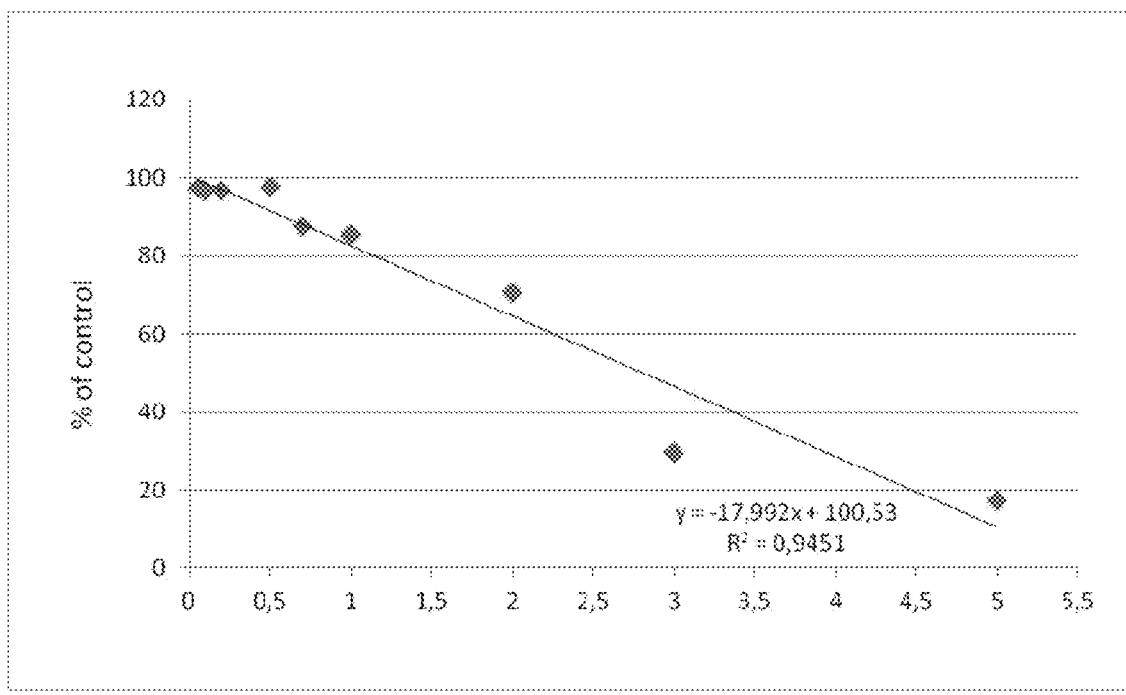
Figure 4C:
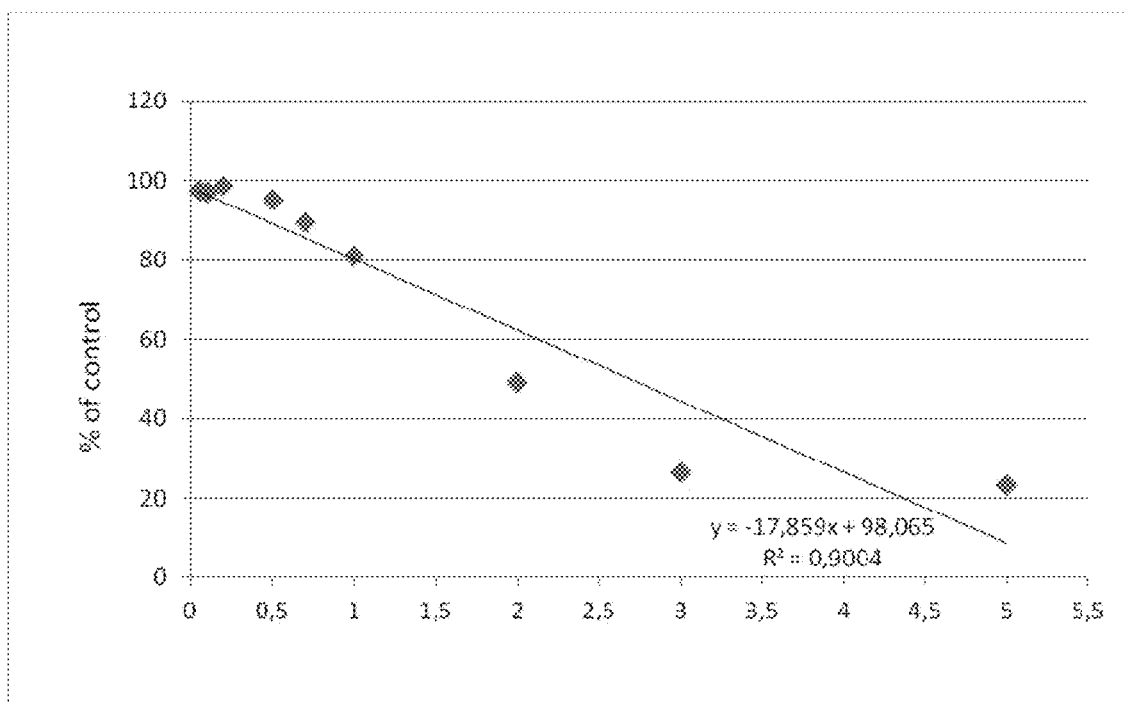
Figure 5A:
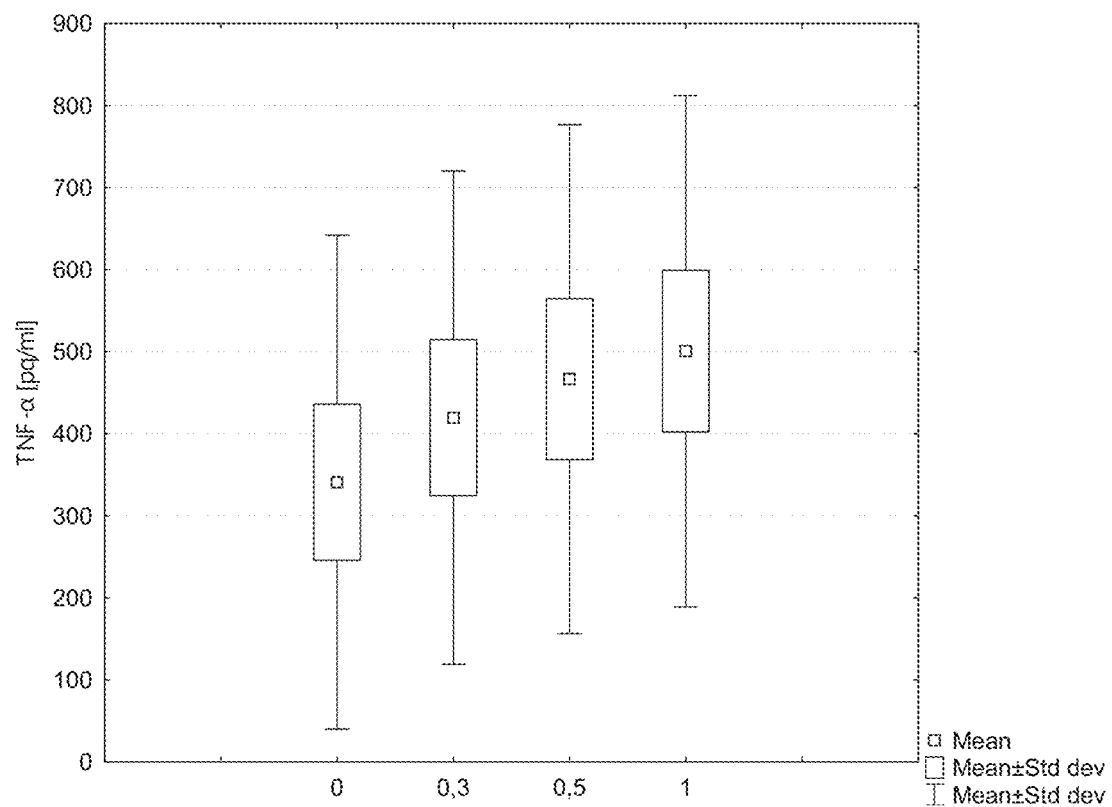
Figure 5B:
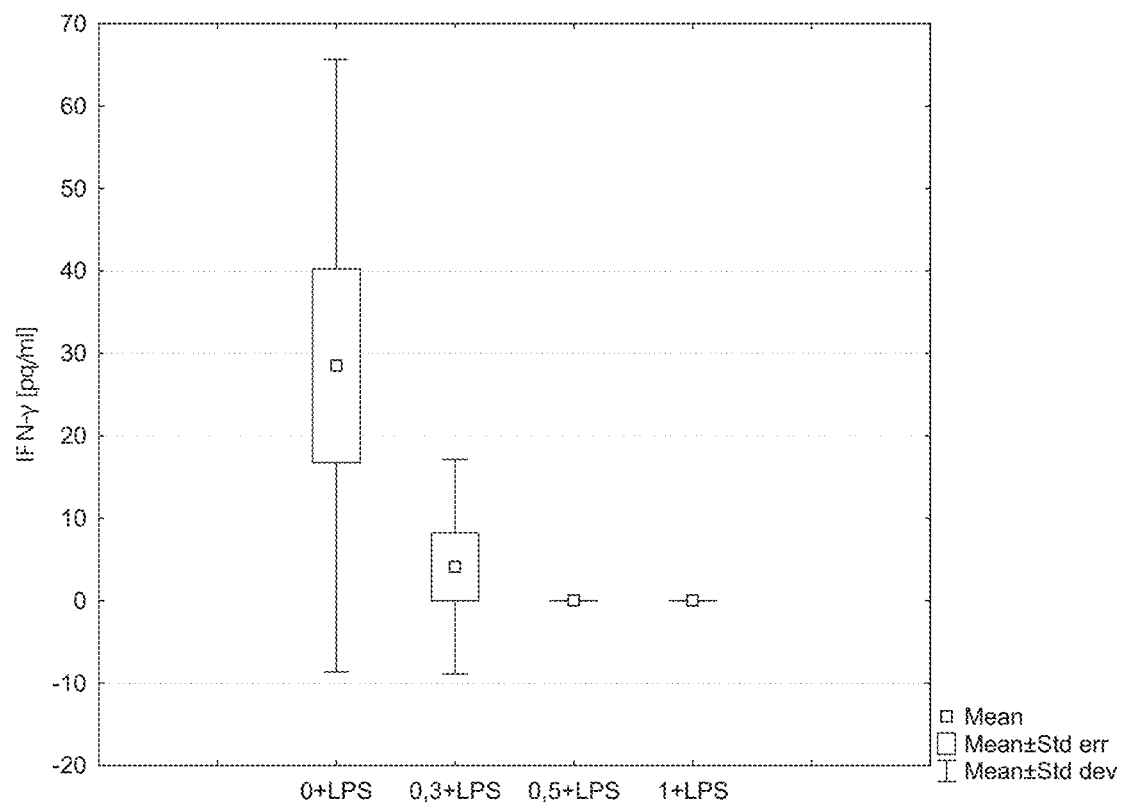

FIG. 1 a diagram showing a treatment of a group of humans (n=10/each) ulcer with (S)-3-[1-Methylpyrrolidin-2-yl]pyridine FIG. 2a a diagram showing a cytotoxicity test with WI-38 cells treated with (S)-3-[1-Methylpyrrolidin-2-yl]pyridine FIG. 2b a diagram showing a cytotoxicity test with A549 cells treated with (S)-3-[1-Methylpyrrolidin-2-yl]pyridine FIG. 2c a diagram showing a cytotoxicity test with HS683 cells treated with (S)-3-[1-Methylpyrrolidin-2-yl]pyridine FIG. 3 a diagram showing a cytotoxicity test of human PBLs treated with (S)-3-[1-Methylpyrrolidin-2-yl]pyridine FIG. 4a a diagram showing the influence of (S)-3-[1-Methylpyrrolidin-2-yl]pyridine on the proliferation of WI-38 cells FIG. 4b a diagram showing the influence of (S)-3-[1-Methylpyrrolidin-2-yl]pyridine on the proliferation of A549 cells FIG. 4c a diagram showing the influence of (S)-3-[1-Methylpyrrolidin-2-yl]pyridine on the proliferation of HS683 cells FIG. 5a a diagram showing the effect of (S)-3-[1-Methylpyrrolidin-2-yl]pyridine on TNF-$\alpha$ production FIG. 5b a diagram showing the effect of (S)-3-[1-Methylpyrrolidin-2-yl]pyridine on IFN-$\gamma$ production In a further example (FIG. 1) the effect of (S)-3-[1-Methylpyrrolidin-2-yl]pyridine is shown. Thereby the healing process of an ulcer is examined as a basic condition. Different ulcers (n=10 for each group) are examined each after 72 h treatment with (S)-3-[1-Methylpyrrolidin-2-yl]pyridine (Group A), treatment with antimicrobians/antimycotics (group B) and without treatment (group C). As a result the treatment with (S)-3-[1-Methylpyrrolidin-2-yl]pyridine resulted in an increased healing effect (group A) compared to the treatment with antimicrobians/antimycotics (group B) and without treatment (group C) (FIG. 1).

In a further example cytotoxicity tests were performed with three different cell lines (FIG. 2a, 2b, 2c):

WI-38 (human diploid cell line from normal embryonic lung tissue)

A549 (human lung adenocarcinoma epithelial cell line) and

HS683 (human neuronal glioma cell line).

Thereby, cell viability was determined on the basis of the mitochondria-dependent reduction of MTT (3-[4,5-dimethyltiazol 2yl]-2,5-diphenyltetrazolium bromide) to formazan. Cell lines ($2 \times 10^5$ cell/ml) as well as leukocytes ($2 \times 10^6$ cells/ml) were cultured in 96-well plates for 48 hours in the presence of various concentrations of (S)-3-[1-Methylpyrrolidin-2-yl]pyridine (5-0.05 mg/ml). Next cells were treated with 20 µl of MTT. After 3 hours of incubation at 37° C., the formazan blue formed in the cells was dissolved in 100 µl of SDS (sodium dodecylsulfate) for 3 hours in 37° C. The optical density was measured on 570 nm.

After the cytotoxicity tests $LC_{50}$ ($LC_{50}$-lethal concentration, 50%-dose required to kill half of the cells after a specified test duration) were estimated for each cell lines and PBLs (leukocytes of peripheral blood). Additionally for PBLs $LC_{10}$ and $LC_5$ were calculated. On the basis of the results for leukocytes three different concentrations of (S)-3-[1-Methylpyrrolidin-2-yl]pyridine were selected for evaluation of the effect of cytokine production.

Further, a proliferation test was prepared for the same three cell lines: WI-38, A549 and HS 683. $3\times10^4$ WI-38 cells and $2\times10^4$ A549 and HS 683. Cells were seeded into each wells in 96-well culture plates in appropriate culture medium with 10% FBS (fetal bovine serum). After 24 h incubation in 37° C./5% $CO_2$ medium were removed and replaced with tested concentrations of (S)-3-[1-Methylpyrrolidin-2-yl]pyridine in culture medium. After 96 hours incubation in 37° C./5% $CO_2$ MTT assay was performed for establishing the cell viability.

Studies of the effect of (S)-3-[1-Methylpyrrolidin-2-yl]pyridine on cytokine production was performed on PBLs isolated ex vivo from 10 healthy volunteers (male 5; female 5; age 23-45). Next, leukocytes were treated with selected, nontoxic concentrations of (S)-3-[1-Methylpyrrolidin-2-yl]pyridine (1 mg/ml; 500 μg/ml, 300 μg/ml) without or with 5 μg/ml of LPS (lipopolysaccharide). After 24 hours of incubation in 37° C./5% $CO_2$ samples of leukocytes and supernatants were collected. For evaluation of the influence of (S)-3-[1-Methylpyrrolidin-2-yl]pyridine on IFN-γ (interferon) production additionally samples were collected after 72 hours of incubation.

Cytokine levels were determined using ELISA kits (BD Biosciences, USA) for human IFNγ, TNF-α and IL-6 and DuoSet for human IL-3 (R&D Systems, USA) according to the producers' instructions. The optical density was measured at 450 nm using a Multiskan RC spectrophotometric reader (Thermo Labsystems, USA), Cytokine concentrations were expressed in pg/ml.

In summary the $LC_{50}$ of (S)-3-[1-Methylpyrrolidin-2-yl]pyridine for a cell line WI-38 is 3.0 mg/ml, for the cell line A549 is 4.5 mg/ml and for the cell line HS-683 is 3.5 mg/ml.

In FIG. 3 the results of the cytotoxicity test of human PBLs is shown.

On the basis of the results of MTT assay for human leukocytes the $LC_{50}$, $LC_{10}$ and $LC_5$ were evaluated. The $LC_{50}$ is a concentration of 7 mg/ml (S)-3-[1-Methylpyrrolidin-2-yl]pyridine. The $LC_{10}$ is in a concentration of 1 mg/ml and $LC_5$ is in a concentration of 0.5 mg/ml (S)-3-[1-Methylpyrrolidin-2-yl]pyridine.

In a further example (FIGS. 4a to 4c) the influence of (S)-3-[1-Methylpyrrolidin-2-yl]pyridine on the proliferation of divers cell lines was investigated. FIG. 3a shows the effect on WI-38 cells. For the cell line WI-38 1.0 mg/ml of (S)-3-[1-Methylpyrrolidin-2-yl]pyridine inhibits 50% of the proliferation of these cells, whereby 4.5 mg/ml inhibits a proliferation of 99%.

For the cell line A549 a concentration of 2.0 mg/ml (S)-3-[1-Methylpyrrolidin-2-yl]pyridine inhibits 50% of the proliferation whereas the concentration of 5.5 mg/ml inhibits 99% of the proliferation.

For the cell line HS-683 2.9 mg/ml (S)-3-[1-Methylpyrrolidin-2-yl]pyridine inhibits 50% of the proliferation of these cells wherein 99% of proliferation are inhibited in a concentration of 5.5 mg/ml.

In another example the cytokine production is evaluated utilizing the effect of (S)-3-[1-Methylpyrrolidin-2-yl]pyridine on TNF-α production. As shown in FIG. 4a the preparation increases the level of cytokines in a dose-dependent manner. The effect was observed only for unstimulated human PBLs.

At the same time studies of the effect of (S)-3-[1-Methylpyrrolidin-2-yl]pyridine on IFN-γ production showed that the preparation strongly decreases the level of interferon in a dose-dependent manner. The effect was observed for LPS stimulated human PBLs. There were poor or no spontaneous IFN-γ production after 24 hours and 72 hours of incubation of PBLs. At the same time no effect of (S)-3-[1-Methylpyrrolidin-2-yl]pyridine was observed for IL-6 production by human PBLs.

Shown in FIGS. 1 to 5 allow cytotoxicity of (S)-3-[1-Methylpyrrolidin-2-yl]pyridine was observed. The preparation inhibits 50% of cell proliferation in doses higher than 1 mg/ml. All other concentrations were harmless. Preparation increased TNF-α production by unstimulated human PBLs in a dose-dependent manner. Further, (S)-3-[1-Methylpyrrolidin-2-yl]pyridine strongly reduces IFN-γ production by LPS-stimulated human PBLs. The effect was again dose-dependent.

Aforesaid discussion of the different embodiments is only carried out by the way of example and does not limit the scope of the protection of the present invention.

The invention claimed is:

1. A method comprising:
   administering to a subject via injection a substance comprising (S)-3-[1-Methylpyrrolidin-2-yl]pyridine, an analog thereof, a precursor thereof, or a derivative thereof, wherein the form of the substance is a colloid comprising fine solid or liquid particles in a fluid, wherein the fluid contains a vehicle substance of saline solution, wherein lactose is used as an additive.

2. The method according to claim 1, wherein the administering comprises injecting the substance by using a syringe and a hollow needle, which is pierced through the skin to a sufficient depth for the material to be administered into the body of the subject.

3. The method according to claim 1, wherein the injection occurs intravenously or intramuscularly.

4. The method according to claim 1, wherein the fluid comprises a liquid carrier, the liquid carrier is at least water or alcohols.

5. The method according to claim 1, wherein the concentration of (S)-3-[1-Methylpyrrolidin-2-yl]pyridine in the substance is 0.3 mg/ml to 4.5 mg/ml.

6. The method according to claim 1, wherein the administration causes stimulation of cholinergic receptors.

7. The method according to claim 1, wherein the subject is a human or animal with a disease related to pain.

8. The method according to claim 7, wherein the diseases is related to a condition selected from the group consisting of obesity, brain inflammation, autoimmune diseases, septic shock, endotoxemia, renal ischemic occlusion and reperfusion, mesenteric occlusion and reperfusion, diabetes, viral related diseases, viral related intoxications, congenital mal formations, cancer, inflammatory diseases, joint pain.

9. The method according to claim 1, wherein the administering is repeated after every 24 hours.

10. The method according to claim 1, wherein administration is performed at a dose of 2 to 3 drops per minute.

11. The method according to claim 1, wherein the administering is performed with a pre-filled syringe.

12. A method comprising:
    preparing a parenteral preparation comprising a substance of (S)-3-[1-Methylpyrrolidin-2-yl]pyridine, an analog, a precursor thereof, or a derivative thereof; and
    sterilizing the parenteral preparation using steam sterilization.

13. The method according to claim 12, wherein the substance is dispensed in at least a single dose.

14. The method according to claim 12, wherein the substance is dissolved in saline solution.

15. The method according to claim 13, wherein the single dosage comprises 100 to 1000 ml.

16. The method according to claim 13, wherein the single dosage comprises 1 to 10 drops per minute.

17. The method according to claim 12, further comprising formulating the parenteral preparation for injection with water as a vehicle.

18. The method according to claim 12, wherein the parenteral preparation is isotonic using sodium chloride.

19. The method according to claim 12, wherein the parenteral preparation further comprises lactose.

20. The method according to claim 1, wherein the substance is dispensed in the form of a parenteral administration into at least a human or animal body.

21. The method according to claim 12, wherein the substance is dispensed in a multi-dose.

22. The method according to claim 17, further comprising formulating the parenteral preparation for injection with a non-aqueous liquid as a vehicle.

23. The method according to claim 17, further comprising formulating the parenteral preparation for injection with water and a non-aqueous liquid as vehicles.

* * * * *